(12) United States Patent
Wu et al.

(10) Patent No.: US 12,196,823 B2
(45) Date of Patent: Jan. 14, 2025

(54) MAGNETIC RESONANCE TEMPERATURE CORRECTION METHOD BASED ON K-SPACE ENERGY SPECTRUM ANALYSIS AND SYSTEM

(71) Applicants: Shanghai Shende Green Medical Era Healthcare Technology Co., Ltd., Shanghai (CN); Shende (Ningbo) Medical Device Technology Co., Ltd, Ningbo (CN); Nantong Shende Medical Device Technology Co., Ltd, Nantong (CN)

(72) Inventors: Hao Wu, Shanghai (CN); Jiabao Wen, Shanghai (CN); Lei Cui, Shanghai (CN); Zhiqiang Su, Shanghai (CN); Huaxin Lu, Shanghai (CN); Zhou Tian, Shanghai (CN); Jian Tao, Shanghai (CN); Haolun Zheng, Shanghai (CN); Xueying Shen, Shanghai (CN); Shenyan Zong, Shanghai (CN)

(73) Assignees: Shanghai Shende Green Medical Era Healthcare Technology Co., Ltd., Shanghai (CN); Shende (Ningbo) Medical Device Technology Co., Ltd, Ningbo (CN); Nantong Shende Medical Device Technology Co., Ltd, Nantong (CN)

( * ) Notice: Subject to any disclaimer, the term of this patent is extended or adjusted under 35 U.S.C. 154(b) by 146 days.

(21) Appl. No.: 18/175,838

(22) Filed: Feb. 28, 2023

(65) Prior Publication Data
US 2023/0204687 A1 Jun. 29, 2023

Related U.S. Application Data

(63) Continuation of application No. PCT/CN2021/082589, filed on Mar. 24, 2021.

(30) Foreign Application Priority Data

Aug. 31, 2020 (CN) .......................... 202010894120.6

(51) Int. Cl.
*G01R 33/00* (2006.01)
*A61N 7/02* (2006.01)
(Continued)

(52) U.S. Cl.
CPC ...... *G01R 33/0082* (2013.01); *G01R 33/0029* (2013.01); *A61N 7/02* (2013.01); *G01R 33/4804* (2013.01); *G01R 33/56563* (2013.01)

(58) Field of Classification Search
CPC ................ G01R 33/00; G01R 33/0023; G01R 33/0029; G01R 33/007; G01R 33/0082;
(Continued)

(56) References Cited

U.S. PATENT DOCUMENTS 5,262,725 A 11/1993 Cuppen et al.
5,742,163 A 4/1998 Liu et al.
(Continued)

FOREIGN PATENT DOCUMENTS

CN 101273891 A 10/2008
CN 102488497 A 6/2012
(Continued)

OTHER PUBLICATIONS

Eibofner et al., Utilizing Echo-Shifts in k-Space for Generation of Positive Contrast in Areas with Marked Susceptibility Alterations, Magnetic Resonance in Medicine, vol. 68, No. 5, pp. 1399-1409, dated Dec. 31, 2012.
(Continued)

*Primary Examiner* — Hoai-An D. Nguyen
(74) *Attorney, Agent, or Firm* — Westbridge IP LLC

(57) ABSTRACT

Disclosed are a magnetic resonance temperature correction method based on k-space energy spectrum analysis and a
(Continued)

system. The method includes: filling a k-space data matrix of magnetic resonance with zeros row by row, and performing an inverse Fourier transform on the k-space data matrix after filling each row of zeros, to obtain a reconstructed image; drawing a pixel intensity variation curve according to a pixel intensity of each pixel in all reconstructed images and a number of rows filled with zeros, and obtaining echo error according to the pixel intensity variation curve, calculation an actual echo time, and calculating a corresponding temperature variation value based on the $\overline{TE}$ of each pixel.

10 Claims, 2 Drawing Sheets

(51) Int. Cl.
    *G01R 33/48* (2006.01)
    *G01R 33/565* (2006.01)
(58) Field of Classification Search
    CPC ........ G01R 33/20; G01R 33/44; G01R 33/48;
                G01R 33/4804; G01R 33/54; G01R
                33/56; G01R 33/565; G01R 33/56563;
                A61N 7/00; A61N 7/02
    USPC ................................ 324/200, 244, 253, 255
    See application file for complete search history.

(56) References Cited

U.S. PATENT DOCUMENTS

| | | | | |
|---|---|---|---|---|
| 7,542,793 | B2* | 6/2009 | Wu | G01R 33/4804 |
| | | | | 600/419 |
| 8,706,190 | B2* | 4/2014 | Gross | G01R 33/4804 |
| | | | | 324/309 |
| 11,354,776 | B2* | 6/2022 | Köhler | G06T 5/00 |
| 2008/0238423 | A1* | 10/2008 | Li | G01R 33/4814 |
| | | | | 324/309 |
| 2008/0292167 | A1 | 11/2008 | Todd et al. | |
| 2010/0217114 | A1* | 8/2010 | Zhou | A61N 7/02 |
| | | | | 600/411 |
| 2011/0046475 | A1* | 2/2011 | Assif | G01R 33/4804 |
| | | | | 600/422 |
| 2014/0088899 | A1 | 3/2014 | Liu et al. | |
| 2017/0011255 | A1 | 1/2017 | Kaditz et al. | |
| 2017/0315257 | A1* | 11/2017 | Coman | G01V 3/32 |
| 2018/0074141 | A1* | 3/2018 | Baumgartl | G01R 33/583 |
| 2021/0199840 | A1* | 7/2021 | Shao | G01V 3/32 |

FOREIGN PATENT DOCUMENTS

| | | | | | |
|---|---|---|---|---|---|
| CN | 102772207 | A | | 11/2012 | |
| CN | 103284722 | A | | 9/2013 | |
| CN | 103403567 | A | | 11/2013 | |
| CN | 103646410 | A | | 3/2014 | |
| CN | 104700440 | A | | 6/2015 | |
| CN | 104749538 | A | | 7/2015 | |
| CN | 106646300 | A | | 5/2017 | |
| CN | 106667487 | A | | 5/2017 | |
| CN | 107468251 | A | | 12/2017 | |
| CN | 109115820 | A | | 1/2019 | |
| CN | 110082696 | A | | 8/2019 | |
| CN | 111568390 | A | | 8/2020 | |
| CN | 112156383 | A | | 1/2021 | |
| CN | 113196080 | A | * | 7/2021 | ............. A61B 5/015 |
| JP | H11108761 | A | * | 4/1999 | ................ G01J 5/48 |
| TW | 201944968 | A | | 12/2019 | |
| TW | I705793 | B | * | 10/2020 | ............. A61B 34/00 |
| WO | 2020142109 | A1 | | 7/2020 | |

OTHER PUBLICATIONS

First Office Action issued in counterpart Chinese Patent Application No. 202010894120.6, dated Mar. 31, 2022.
International Search Report and Written Opinion issued in corresponding PCT Application No. PCT/CN2021/082589, dated Jun. 23, 2021.
Chen et al, Application of k-space energy spectrum analysis to susceptibility field mapping and distortion correction in gradient-echo EPI, Neuroimage, Elsevier, Amsterdam, NL, vol. 31, No. 2, pp. 609-622, dated Jun. 1, 2006.
Extended European Search Report issued in counterpart Europe Patent Application No. 21859560.1, dated Aug. 27, 2024.
Zong et al., Improved PRF-based MR thermometry using k-space energy spectrum analysis, Magnetic Resonance in Medicine, vol. 84, No. 6, pp. 3325-3332, dated Jun. 25, 2020.

* cited by examiner

MAGNETIC RESONANCE TEMPERATURE CORRECTION METHOD BASED ON K-SPACE ENERGY SPECTRUM ANALYSIS AND SYSTEM

CROSS-REFERENCE TO RELATED APPLICATIONS

This application is a continuation application of International Application No. PCT/CN2021/082589, filed on Mar. 24, 2021, which claims priority to Chinese Patent Application No. 202010894120.6, filed on Aug. 31, 2020. The disclosures of the above-mentioned applications are incorporated herein by reference in their entireties.

TECHNICAL FIELD

The present application relates to a magnetic resonance temperature measurement technique, and in particular to a magnetic resonance temperature correction method based on k-space energy spectrum analysis and system.

BACKGROUND

Magnetic resonance-guided phase-controlled focused ultrasound is a non-invasive treatment for thermal ablation of uterine fibroids, idiopathic tremor, and other diseases. In the system, focused ultrasound uses the tissue penetration of ultrasound to focus multiple beams of ultrasound on the treated area to produce a temperature at the focal point that is sufficient to kill the cells to achieve the treatment. Magnetic resonance scanning can image the focal point level and obtain information on the variation in tissue properties caused by temperature to measure the actual temperature to monitor the entire thermal treatment process and ensure the safety of the treatment. Currently, the magnetic resonance temperature measurement based on proton resonance frequency variation is widely used for temperature monitoring of thermal treatments in clinical settings. Research shows that the variation in temperature cause variation in the resonance frequency of hydrogen nuclei (i.e., protons), and the resonance frequency shifts by about 1.28 Hz for increase of each 1° C. in temperature at a magnetic field strength of 3T. Combined with the echo time TE of imaging, the final temperature variation information can be mapped to the phase diagram of magnetic resonance, i.e., the offset of the resonance frequency multiplied by the echo time TE represents the phase variation of the focal position in the image. The phase variation of the image corresponds to the temperature, and the phase map obtained from the Magnetic resonance scanning can help measure the temperature variation. The echo time TE plays a very important role in the temperature measurement method, and an accurate echo time can help to obtain the correct temperature variation.

However, the echo time TE is susceptible to the inhomogeneity of the magnetic resonance main magnetic field B0, which is reflected in the presence of locally varying field strength gradients on the image, and the field strength gradients of the magnetic strength are represented as spatially distributed phase gradients on the magnetic resonance phase diagram. According to the frequency-shifted nature of the Fourier transform, the gradient variation of the phase in the spectrum is represented as a shift in the center of the spectrum. Therefore, in the k-space of magnetic resonance, this inhomogeneity of B0 causes a shift in the center of the k-space echo. Theoretically, the echo time TE entered by the user when operating the magnetic resonance machine should correspond to the center of echo in k-space, but due to the inhomogeneity of B0, the center of echo in k-space will deviate from theoretical center of echo, i.e., the actual echo time TE will not be equal to the value preset by the user. In this case, if theoretical TE value is used in the temperature calculation, the measured temperature will be wrong.

The current methods for solving the above problem are that the correction method based on the field strength gradient map and the correction method based on the magnetic resonance two-way echo sequence, which requires reprogramming of the conventional scanning sequence and is tedious. The correction method based on the field strength gradient map does not perform well in terms of noise robustness compared with the present method.

SUMMARY

The purpose of the present application is to overcome the above-mentioned defects of the prior art and provide a magnetic resonance temperature correction method based on k-space energy spectrum analysis, which has a simple calculation and a high efficiency and a good robustness.

The purpose of the present application is achieved by the following technical solution.

The present application provides a magnetic resonance temperature correction method based on k-space energy spectrum analysis, including:

filling a k-space data matrix of magnetic resonance with zeros row by row along a frequency encoding direction or a phase encoding direction, where an encoding number of the k-space is 64, 128 or 256, and performing an inverse Fourier transform on the k-space data matrix after filling each row of zeros, to obtain a reconstructed image;

drawing a pixel intensity variation curve according to a pixel intensity of each pixel in all reconstructed images and a number of rows filled with zeros, wherein the number of rows filled with zeros at 50% reduction of the pixel intensity of pixels is $n_1$, and a number of rows located in the middle of the k-space data matrix is $n_0$, and correcting echo time TE of sequence to obtain actual echo time $\overline{TE}$, a correction formula is:

$$\overline{TE} = TE + \Delta TE$$

$$\Delta TE = \frac{1}{BW} \times \Delta n$$

$$\Delta n = n_1 - n_0$$

where BW is a bandwidth, $\Delta n$ is a difference of the number of rows, and $\Delta TE$ is an echo error; and calculating a corresponding corrected temperature variation value $\Delta T$ based on the $\overline{TE}$ of each pixel.

The variation in proton resonance frequency is directly expressed as the variation in phase on the reconstructed image, and the temperature variation is calculated from the phase variation, the $\Delta T$ is calculated by a formula:

$$\Delta T = \frac{\Delta \varphi}{\alpha \cdot \gamma \cdot B_0 \cdot \overline{TE}}$$

where $\Delta \varphi$ is a phase difference, $\alpha$ is a proton resonance frequency variation coefficient, $B_0$ is a magnetic induction intensity of a main magnetic field, and $\gamma$ is a hydrogen proton spin-to-magnetic ratio.

The present application provides a magnetic resonance temperature correction system based on k-space energy spectrum analysis, including:
- an image reconstruction module for filling a k-space data matrix of magnetic resonance with zeros row by row along a frequency encoding direction or a phase encoding direction, where the encoding number of the k-space is 64, 128 or 256, and performing an inverse Fourier transform on the k-space data matrix after filling each row of zeros, to obtain a reconstructed image;
- a curve drawing module for drawing a pixel intensity variation curve according to a pixel intensity of each pixel in all reconstructed images and a number of rows filled with zeros, and obtaining echo time ΔTE based on the curve;
- an error correction module for correcting echo time TE of sequence according to the ΔTE to obtain actual echo time $\overline{TE}$; and
- a temperature difference calculation module for calculating a corresponding corrected temperature variation value ΔT based on the TE of each pixel;

wherein a correction formula is:

$$\overline{TE} = TE + \Delta TE$$

$$\Delta TE = \frac{1}{BW} \times \Delta n$$

$$\Delta n = n_1 - n_0$$

where $n_1$ is a number of rows filled with zeros at 50% reduction of pixel intensity of the pixels, $n_0$ is a number of rows located in the middle of the k-space data matrix, BW is a bandwidth, and Δn is a difference of the number of rows.

In an embodiment, the ΔT is calculated by a formula:

$$\Delta T = \frac{\Delta \varphi}{\alpha \cdot \gamma \cdot B_0 \cdot \overline{TE}}$$

where Δφ is a phase difference, α is a proton resonance frequency variation coefficient, $B_0$ is a magnetic induction intensity of a main magnetic field, and γ is a hydrogen proton spin-to-magnetic ratio.

Compared with the prior art, the present application has the following beneficial effects.

The present application fills zeros row by row on the k-space data matrix, then performs an inverse Fourier transform to obtain the reconstructed image, draws the pixel intensity variation curve, obtains the echo error according to the curve, and uses it to correct the echo time to obtain the actual echo time, and calculates the temperature variation according to the actual echo time. The present application is easy and efficient to calculate, and does not reduce the temporal resolution of magnetic resonance scanning, and has stronger robustness and wide application range when applied to images with multiple noises.

DETAILED DESCRIPTION OF THE EMBODIMENTS

The present application is described in detail below in conjunction with the attached drawings and specific embodiments. The embodiments are implemented on the premise of the technical solution of the present application, and detailed implementation and specific operation procedures are given, but the scope of the present application is not limited to the following embodiments.

Embodiment 1

Figure 1:
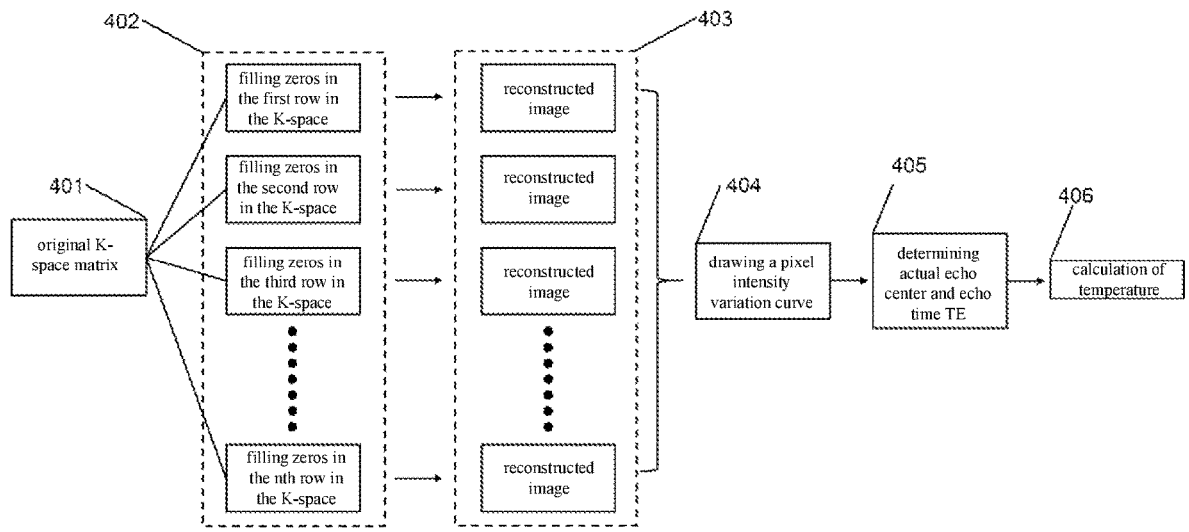
FIG. 1 is a flowchart of the method according to the present application.

The present application provides a magnetic resonance temperature correction method based on k-space energy spectrum analysis, as shown in FIG. 1, the method includes:
- 401, magnetic resonance scanning a layer where the focal point is located to obtain the original k-space data matrix;
- 402, filling the k-space data matrix of magnetic resonance with zeros row by row along a frequency encoding direction or a phase encoding direction, where an encoding number of the k-space is 64, 128 or 256;
- 403, performing an inverse Fourier transform on the filled k-space data matrix after filling each row of zeros, to obtain a reconstructed image;
- 404, drawing a pixel intensity variation curve according to a pixel intensity of each pixel in all reconstructed images and a number of rows filled with zeros, wherein the number of rows filled with zeros at 50% reduction of the pixel intensity of pixels is $n_1$, and a number of rows located in the middle of the k-space data matrix is $n_0$;
- 405, calculating the actual echo time $\overline{TE}$, where a calculation formula is:

$$\overline{TE} = TE + \Delta TE$$

$$\Delta TE = \frac{1}{BW} \times \Delta n$$

$$\Delta n = n_1 - n_0$$

where BW is a bandwidth, Δn is a difference of the number of rows, and ΔTE is an echo error;
- 406, calculating a corresponding temperature variation value ΔT based on the $\overline{TE}$ of each pixel.

The temperature measurement of magnetic resonance is mainly imaged by the variation of characteristics of tissue parameters subject to temperature variation, and the response of variation of these parameters on the image is used to map the temperature variation, and the variation of proton resonance frequency is directly expressed as the variation of phase on the reconstructed image. Under 3T magnetic field strength, each 1° C. temperature variation can cause a resonance frequency variation of 1.28 Hz, and the temperature variation is calculated according to the phase variation. The formula for calculating the ΔT is $$\Delta T = \frac{\Delta \varphi}{\alpha \cdot \gamma \cdot B_0 \cdot \overline{TE}}$$

where Δφ is a phase difference, α is a proton resonance frequency variation coefficient, $B_0$ is a magnetic induction intensity of a main magnetic field, and γ is a hydrogen proton spin-to-magnetic ratio.

Figure 2:
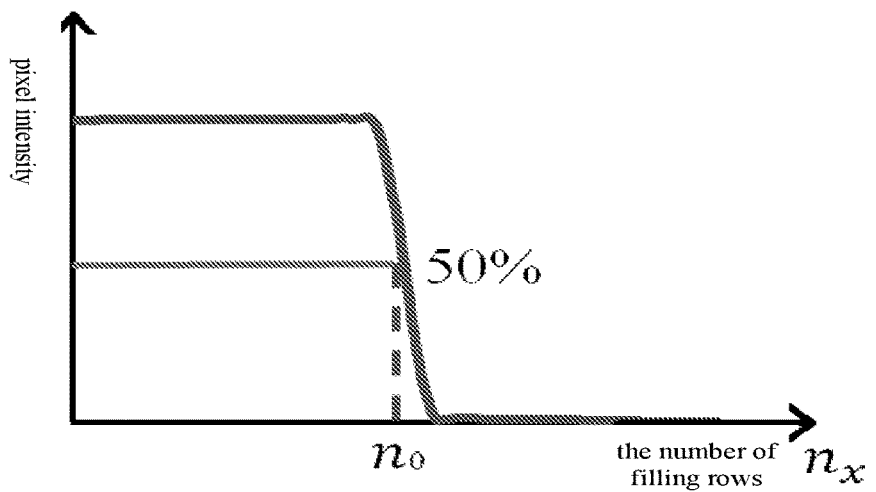
FIG. 2 is a diagram of the pixel intensity variation curve under a uniform magnetic field.

As shown in FIG. 1, the center of echo is the pixel with the highest pixel intensity in k-space, and ideally the magnetic field is perfectly homogeneous, as shown in FIGS. 2, the k-space energy spectrum is analyzed, the center of echo is located at the center of k-space, and the position at 50% reduction of the pixel intensity is at the center of k-space, i.e., the row filled with zeros is located exactly in the middle of the k-space data matrix.

Figure 3:
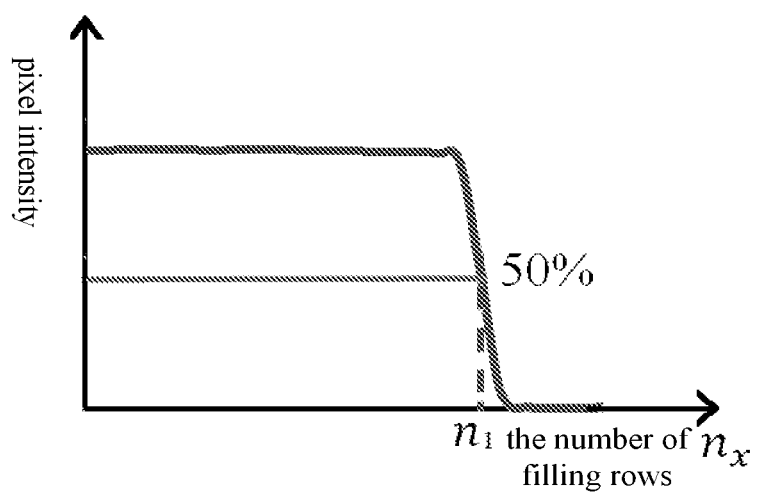
FIG. 3 is the pixel intensity variation curve under a non-uniform magnetic field.

As shown in FIG. 3, the space is provided with a gradient magnetic field of 0.308 mT/m, and the gradient changing magnetic field on the space will cause the echo shift, and the center of echo is deviated from the center of k-space, and there is a clear shift at the 50% reduction of pixel intensity, i.e., ΔTE.

Embodiment 2

The present application provides a magnetic resonance temperature correction system based on k-space energy spectrum analysis corresponding to embodiment 1, including:

an image reconstruction module for filling zeros row by row on the k-space data matrix along a frequency encoding direction or a phase encoding direction, filling zeros row by row along the frequency encoding direction, i.e., in the gradient echo sequence, and filling zeros row by row along the phase encoding direction, i.e., in the plane echo sequence, where an encoding number of the k-space is 128.

filling the k-space data matrix of the magnetic resonance with zeros row by row, and performing an inverse Fourier transform on the filled k-space data matrix after filling each row of zeros, to obtain a reconstructed image, and finally obtain 128 new k-space images and 128 reconstructed images;

a curve drawing module for drawing a pixel intensity variation curve based on the pixel intensity of each pixel in all reconstructed images and the number of rows filled with zeros, and obtaining an echo error ΔTE based on the curve;

an error correction module, for correcting the echo time TE of the sequence according to the ΔTE, to obtain the actual echo time $\overline{TE}$;

a temperature difference calculation module, for calculating a temperature variation value ΔT corresponding to each pixel based on the $\overline{TE}$;

the $\overline{TE}$ is calculated by the formula $$\overline{TE} = TE + \Delta TE$$

$$\Delta TE = \frac{1}{BW} \times \Delta n$$

$$\Delta n = n_1 - n_0$$

where $n_1$ is a number of rows filled with zeros at 50% reduction of pixel intensity of the pixels, $n_0$ is a number of rows located in the middle of the k-space data matrix, BW is a bandwidth, and Δn is a difference of the number of rows.

In an embodiment, the ΔT is calculated by the formula:

$$\Delta T = \frac{\Delta \varphi}{\alpha \cdot \gamma \cdot B_0 \cdot \overline{TE}}$$

where Δφ is a phase difference, α is a proton resonance frequency variation coefficient, $B_0$ is a magnetic induction intensity of a main magnetic field, and γ is a hydrogen proton spin-to-magnetic ratio.

The embodiment 1 and embodiment 2 provide a magnetic resonance temperature correction method based on k-space energy spectrum analysis and system, which calculate the actual center of echo position and position offset size of each pixel on the image, and then calculate the deviation of the echo time of each pixel in space, the actual echo time in space being equal to the sum of the echo time TE of the sequence and the deviation of the echo time, and use the actual echo time to calculate the temperature, to thus obtain the correct temperature variation, to achieve the temperature correction.

The above describes in detail a specific embodiment of the present application. It should be understood that those skilled in the art can make many modifications and variations according to the idea of the present application without creative work. Therefore, any technical solution that can be obtained by logical analysis, reasoning or limited experiments based on the prior art by those skilled in the art in accordance with the idea of the present application shall be within the scope determined by the claims.

What is claimed is:

1. A magnetic resonance temperature correction method based on k-space energy spectrum analysis, comprising:

filling a k-space data matrix of magnetic resonance with zeros row by row, and performing an inverse Fourier transform on the k-space data matrix after filling each row of zeros, to obtain a reconstructed image;

drawing a pixel intensity variation curve according to a pixel intensity of each pixel in all reconstructed images and a number of rows filled with zeros, wherein the number of rows filled with zeros at 50% reduction of the pixel intensity of pixels is $n_1$, and a number of rows located in the middle of the k-space data matrix is $n_0$, and correcting echo time TE of sequence to obtain actual echo time $\overline{TE}$, a correction formula is:

$$\overline{TE} = TE + \Delta TE$$

$$\Delta TE = \frac{1}{BW} \times \Delta n$$

$$\Delta n = n_1 - n_0$$

wherein BW is a bandwidth, Δn is a difference of the number of rows, and ΔTE is an echo error; and calculating a corresponding corrected temperature variation value ΔT based on the $\overline{TE}$ of each pixel.

2. The method according to claim 1, wherein $\Delta T$ is calculated by a formula:

$$\Delta T = \frac{\Delta \varphi}{\alpha \cdot \gamma \cdot B_0 \cdot \overline{TE}}$$

wherein $\Delta \varphi$ is a phase difference, $\alpha$ is a proton resonance frequency variation coefficient, $B_0$ is a magnetic induction intensity of a main magnetic field, and $\gamma$ is a hydrogen proton spin-to-magnetic ratio.

3. The method according to claim 1, wherein the zeros are filled row by row on the k-space data matrix along a frequency encoding direction.

4. The method according to claim 1, wherein the zeros are filled row by row on the k-space data matrix along a phase encoding direction.

5. The method according to claim 1, wherein an encoding number of the k-space is 64, 128 or 256.

6. A magnetic resonance temperature correction system based on k-space energy spectrum analysis, comprising:
an image reconstruction module for filling a k-space data matrix of magnetic resonance with zeros row by row, and performing an inverse Fourier transform on the k-space data matrix after filling each row of zeros, to obtain a reconstructed image;
a curve drawing module for drawing a pixel intensity variation curve according to a pixel intensity of each pixel in all reconstructed images and a number of rows filled with zeros, and obtaining echo time $\Delta TE$ based on the curve;
an error correction module for correcting echo time TE of sequence according to the $\Delta TE$ to obtain actual echo time $\overline{TE}$; and
a temperature difference calculation module for calculating a corresponding corrected temperature variation value $\Delta T$ based on the $\overline{TE}$ of each pixel;

wherein a correction formula is:

$$\overline{TE} = TE + \Delta TE$$

$$\Delta TE = \frac{1}{BW} \times \Delta n$$

$$\Delta n = n_1 - n_0$$

wherein $n_1$ is a number of rows filled with zeros at 50% reduction of pixel intensity of the pixels, $n_0$ is a number of rows located in the middle of the k-space data matrix, BW is a bandwidth, and $\Delta n$ is a difference of the number of rows.

7. The system according to claim 6, wherein $\Delta T$ is calculated by a formula:

$$\Delta T = \frac{\Delta \varphi}{\alpha \cdot \gamma \cdot B_0 \cdot \overline{TE}}$$

where $\Delta \varphi$ is a phase difference, $\alpha$ is a proton resonance frequency variation coefficient, $B_0$ is a magnetic induction intensity of a main magnetic field, and $\gamma$ is a hydrogen proton spin-to-magnetic ratio.

8. The system according to claim 6, wherein the image reconstruction module is configured for filling zeros row by row on the k-space data matrix along a frequency encoding direction.

9. The system according to claim 6, wherein the image reconstruction module is configured for filling zeros row by row on the k-space data matrix along a phase encoding direction.

10. The system according to claim 6, wherein an encoding number of the k-space is 64, 128 or 256.

* * * * *